United States Patent [19]

Kawamura

[11] Patent Number: 5,310,618
[45] Date of Patent: May 10, 1994

[54] LIGHT-SENSITIVE COMPOSITIONS AND ARTICLES UTILIZING A COMPOUND OR POLYMER CONTAINING AN AROMATIC DIAZONIUM SALT GROUP AND A LIGHT-ABSORBING RESIDUE OF A SENSITIZING DYE FOR TRICHLOROMETHYL-S-TRIAZINE OR AZINIUM SALT PHOTOPOLYMERIZATION INITIATORS

[75] Inventor: Kouichi Kawamura, Shizuoka, Japan

[73] Assignee: Fuji Photo Film Co., Ltd., Minami-ashigara, Japan

[21] Appl. No.: 705,360

[22] Filed: May 24, 1991

[30] Foreign Application Priority Data

May 31, 1990 [JP] Japan .................................. 2-142947

[51] Int. Cl.$^5$ ...................... G03F 7/016; G03F 7/021
[52] U.S. Cl. .................................. 430/157; 430/171; 430/175; 430/176; 430/281; 430/285; 430/919; 430/920; 534/558; 534/561
[58] Field of Search ............... 430/171, 175, 519, 520, 430/521, 522, 919, 920, 176, 281, 157, 285; 534/558, 559, 560, 561, 562, 563, 564

[56] References Cited

U.S. PATENT DOCUMENTS

| | | | |
|---|---|---|---|
| 3,778,270 | 12/1973 | Roos | 430/171 |
| 4,400,458 | 8/1983 | Walkow et al. | 430/171 |
| 4,687,728 | 8/1987 | Folkard et al. | 430/171 |
| 4,914,000 | 4/1990 | Dhillon | 430/171 |
| 4,946,373 | 8/1990 | Walls et al. | 430/281 |
| 4,956,262 | 9/1990 | Schlosser et al. | 430/281 |

Primary Examiner—Charles L. Bowers, Jr.
Assistant Examiner—Christopher G. Young
Attorney, Agent, or Firm—Burns, Doane, Swecker & Mathis

[57] ABSTRACT

A light-sensitive composition comprising either an alkali-soluble resin or radical-polymerizable, unsaturated compound, and a diazonium compound represented by general formula (I) or (II):

$$(S)_l-(L^1)_m-(D)_n \quad (I)$$

$$-(L^2(S))_o-(L^3(D))_p- \quad (II)$$

wherein D is a diazonium salt group, S is a light absorbing group, $L^1$, $L^2$ and $L^3$ are connecting groups connecting S and D, provided that S and D are not conjugated by $L^1$, $L^2$ and $L^3$; l, m, n, o and p are integers.

25 Claims, No Drawings

LIGHT-SENSITIVE COMPOSITIONS AND ARTICLES UTILIZING A COMPOUND OR POLYMER CONTAINING AN AROMATIC DIAZONIUM SALT GROUP AND A LIGHT-ABSORBING RESIDUE OF A SENSITIZING DYE FOR TRICHLOROMETHYL-S-TRIAZINE OR AZINIUM SALT PHOTOPOLYMERIZATION INITIATORS

BACKGROUND OF THE INVENTION

The present invention relates to a light-sensitive composition which is spectrally sensitized and highly sensitive in a broad wavelength region from the ultraviolet region to the visible region, and comprises a novel aromatic diazonium compound.

Aromatic diazonium compounds have come to be used in various light-sensitive compositions. For example, their photodecomposability has been utilized in combination with couplers in dye image formation, and, their photocrosslinkability or light induced insolubility has been widely used with monomers or binders in the field of lithographic plates, proof mask films, and resists. The use of these kinds of light-sensitive compositions is given in J. Kosar, *Light Sensitive Systems* (John Wiley & Sons, 1965), and A. Reiser, *Photoreactive Polymers* (John Wiley & Sons, 1989).

However, with respect to light sensitive compositions utilizing aromatic diazonium compounds, no system has yet been proposed having high light-sensitivity from the ultraviolet to the visible wavelength region.

In the above light-sensitive compositions, the photodecomposable aromatic diazonium compounds generally require very great energies to photodecompose, and their light-sensitive wavelengths are equal to or shorter than wavelengths of the blue portion of the visible spectrum. For this reason the scope of light-sensitive compositions which can be used ends with low sensitivity materials and those which are exposed with ultraviolet rays.

For these reasons, vigorous research has been applied to photosensitization in the visible region of photodecomposable aromatic diazonium compounds. For example, it is known that specific dyes having riboflavin, porphyrin, chlorophyl, etc. are spectral sensitizers. Other sensitization methods are proposed by E. Inoue in "Photographic Science and Engineering", volume 17, pages 28 and 268, and volume 18, page 25, in which systems are proposed having a mixture of sensitizing color elements, such as methylene blue, etc., and p-toluene sulphonic acid, among other activators.

However, present methods, because they have such defects as not yet having sufficient sensitivity, having poor stability, not allowing free selection of the spectral wavelength region, etc., have not arrived at the stage where they can actually be incorporated into products.

SUMMARY OF THE INVENTION

It is therefore an object of the present invention to offer a light-sensitive composition including a novel aromatic diazonium compound having high spectral sensitization from the ultraviolet region to the visible region.

In accordance with the above object, the present invention provides a diazonium compound selected from compounds of the following formulas:

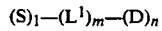

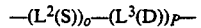

wherein D is a diazonium salt group, S is a light absorbing group, $L^1$, $L^2$ and $L^3$ are connecting groups, and l, m, n, o and p are integers; and
wherein $L^1$, $L^2$ and $L^3$ do not conjugate S and D.

According to a preferred embodiment of the present invention, S is selected from merocyanine dyes, cyanine dyes, acridine dyes, multi nucleus aromatic compounds, xanthene dyes, coumarin dyes and hetero aromatic compounds.

In another preferred embodiment of the present invention, S is a compound of the following formula:

In formula (III), R is a substituted or unsubstituted, aromatic or hetero aromatic group having from 6 to 20 carbon atoms. $G^1$ and $G^2$ are the same or different and each may represent a hydrogen atom, cyano, alkoxy carbonyl, substituted alkoxy carbonyl, aryloxy carbonyl, substituted aryloxy carbonyl, aryloxy carbonyl, substituted aryloxy carbonyl, acyl, substituted acyl, aryl carbonyl, substituted aryl carbonyl, alkyl thio, aryl thio, alkyl sulfonyl, aryl sulfonyl or fluoroalkyl sulfonyl, provided that $G^1$ and $G^2$ may not both be hydrogen. $G_1$ and $G^2$ may combine to form a ring comprising nonmetallic atoms together with a carbon atom to which they are bonded. The variable n is 0 or 1.

D in the above formulas (I) and (II) is preferably selected from benzene diazonium salt, naphthalene diazonium salt, biphenyl diazonium salt, anthraquinone diazonium salt; and wherein D may be substituted with alkoxy, substituted thiol, substituted amino, carboalkoxy, or halogen.

Other embodiments of the present invention provide a light-sensitive composition containing the novel diazonium compound of formulas (I) and (II) and either (1) an alkali soluble polymer, or (2) a radical polymerizable unsaturated compound.

Further objects, features and advantages of the present invention will become apparent from the Detailed Description of the Preferred Embodiments which follows, when read in light of the Working and Comparative Examples.

DETAILED DESCRIPTION OF THE PREFERRED EMBODIMENTS

In order to efficiently spectrally sensitize an aromatic diazonium compound, it is necessary to efficiently transfer light energy from the light-absorbed sensitizing dye to the diazonium salt. Whichever of the two methods of light transfer is used, either energy transfer or electron transfer, it is important, in order to improve the efficiency of the transfer, to satisfy at least the following three conditions.

1. That the excitation lifespan of the sensitizing dye is long.
2. That there is an appropriate relationship between the potential energy or redox potentials of the excited dye and the diazonium salt.
3. That the physical separation between the dye and diazonium salt molecules is small.

The third point is not a problem in a solution to the degree that there are collisions due to diffusion movement, however, in coating systems in which the light sensitive compositions are actually used, it becomes an important factor because the diffusion movement is extremely limited. In other words, it is important, in order for the energy transfer between the dye and the diazonium compound to take place efficiently, that the dye and the diazonium compound to be at close separation beforehand.

The above point is described in N. J. Turro, *Modern Molecular Photochemistry*, chapter 9 (1978) Benjamin/Cummings Publishing Co. and in N. J. Turro "Chemical Review", volume 86, pages 401-449 (1986), and in the essay starting from page 161 in M. A. Fox, M. Chanon, eds., *Photoinduced Electron Transfer*, Part A (1988).

The present inventors, in order to make the spectral sensitization of aromatic diazonium salts more efficient, have conducted vigorous research taking into account the above factors, and, as a result, have arrived at the discovery that specific diazonium salts possess high sensitivity from the ultraviolet to the visible region.

The objects of the present invention can be attained by the use of a novel diazonium salt having in a molecule at least one aromatic diazonium salt portion and at least one light absorbing portion which is not the same conjugated chromophoric group as the diazonium salt portion.

The novel diazonium salt of the present invention can be described by the compound to which a light absorbing portion and an aromatic diazonium salt are attached as in general formula (I), or by the polymeric compound containing light absorbing portions and aromatic diazonium portions as components in the form of general formula (II).

$$(S)_l—(L^1)_m—(D)_n \quad (I)$$

$$—(L^2(S))_o—(L^3(D))_p— \quad (II)$$

wherein D is a diazonium salt group, S is a light group, $L^1$, $L^2$ and $L^3$ are connecting groups connecting S and D. However, S and D are not conjugated by $L^1$, $L^2$ and $L^3$. The variables l, m, n, o and p are integers.

The chromophore used as a light absorbing portion is preferably a light-absorbing residue which has an absorption coefficient of more than 1000 at wavelengths longer than 300 nm. Such light absorbing compounds can be dyes presently used as sensitizing dyes for trichloromethyl-s-triazine photopolymerization initiators and azinium salt photopolymerization initiators.

Specific examples are the merocyanine dyes disclosed in U.S. Pat. Nos. 4,481,276, 4,399,211 and 4,810,618; the cyanine dyes disclosed in DE-A 3,541,534 and Japanese Unexamined Laid-open Application (hereinafter J.P.KOKAI) No. Sho 58-29803, etc.; the acridine dyes, such as acridine orange, etc., disclosed in U.S. Pat. No. 4,845,011; thiapyrylium dyes, such as 4-(4-methoxyphenyl)-2,6-diphenyl thiapyrylium salts, etc., disclosed in J.P.KOKAI No. Sho 58-40302; arylidene dyes disclosed in (J.P.KOKAI No. Sho 47-13103 and cyanine dyes having an oxo-carbon bridge nucleus such as squalylium, etc.; as well as multi-nucleus aromatic compounds such as 9,10-diethyl anthracene, pyrene; xanthene dyes such as eosine, erythrocine and fluorescein, which are disclosed along with cyanine, merocyanine and acridine dyes in U.S. Pat. Nos. 4,743,529, 4,743,530 and 4,743,531. Also used are coumarine compounds disclosed in U.S. Pat. No. 4,743,531, and Research Disclosure, volume 200, December 1980, item 20036. Additionally used are hetero aromatic compounds such as acridone and thioxanthone, Michler's ketone, amino aromatic compounds such as polyaryl amine and amino-substituted chalcone, porphyrin dyes and phthalocyanine dyes.

Particularly preferred examples are merocyanine dyes, cyanine dyes, acridine dyes, multi-nucleus aromatic compounds, xanthene dyes, coumarine dyes, hetero aromatic compounds, as well as arylidene dyes of the following general formula (III).

$$R—(CH=CH)_n—CH=C(G^1)(G^2) \quad (III)$$

In the formula, R represents a substituted or unsubstituted aromatic ring, or a heteroaromatic ring having 6 to 20 carbon atoms. Substituents may be alkyl groups, aryl groups, and, in addition they may also be alkylamino, dialkylamino, arylamino, diarylamino, alkylthio, aryloxy, alkoxy, hydroxy, acyloxy, carboxyl, carboalkoxy, carboaryloxy, acyl, sulfonyl and sulfonylamido groups.

$G^1$ and $G^2$ may be the same or different and each may represent a hydrogen atom, a cyano group, an alkoxy carbonyl group, a substituted alkoxy carbonyl group, an aryloxy carbonyl group, a substituted aryloxy carbonyl group, an acyl group, a substituted acyl group, an aryl carbonyl group, a substituted aryl carbonyl group, an alkylthio group, an arylthio group, an alkyl sulfonyl group, an aryl sulfonyl group or a fluoroalkyl sulfonyl group. However, $G^1$ and $G^2$ are not hydrogen atoms at the same time. In addition, $G^1$ and $G^2$ may also be in the form of a ring of carbon atoms bound together with non-metallic elements.

If $G^1$ and $G^2$ are in the form of rings of carbon atoms bound together with non-metallic elements, the ring is usually an acidic nucleus used in merocyanine dyes, for example, barbituric acid nuclei such as 1,3-diethyl-2-thiobarbituric acid and rhodanine nuclei such as 3-ethyl rhodanine.

The variable n is 0 or 1.

When an arylidene residue according to general formula (III) is used as the light-absorbing portion of the novel aromatic diazonium compound of the present invention, at least one of R, $G^1$ and $G^2$ must have at least one functional group necessary for forming the connecting group L which connects the aromatic diazonium salt portion. Such groups are for example, a carboxyl group, a hydroxyl group, an amino group, a sulfonyl group, an isocyanate group, a thioisocyanate group or a thiol group.

One may use as the aromatic diazonium salt portions designated by D diazonium salts named in in J. Kosar, *Light Sensitive Systems* (John Wiley & Sons, Inc. 1965), chapter 6 and chapter 7. Examples that can be named are benzenediazonium salt, naphthalene diazonium salt, biphenyldiazonium salt, anthraquinone diazonium salt, etc. These diazonium salts can be substituted with, for example, alkoxy groups such as methoxy, ethoxy and butoxy, substituted thiol groups such as methylthio and phenylthio, amino groups such as dimethylamino, diethylamino and phenylamino, carboalkoxy groups such as carbomethoxy and halogen atoms.

These aromatic diazonium salts used in the present invention must contain at least one functional group necessary for forming the bonds $L^1$, $L^2$ and $L^3$ which connect the light-absorbing portion and the aromatic diazonium salts, for example, a carboxyl group, a hydroxyl group, an amino group, a sulfonyl group, an isocyanate group or a thiocyanate group.

The variables $L^1$, $L^2$ and $L^3$ are connecting groups which connect S and D through a covalent bond. However, S and D are not directly conjugated. Included in the connecting groups represented by $L^1$, $L^2$ and $L^3$, one can name the following bonding components: ester bonds (—CO₂—), amido bonds (—CONH—), urea bonds (—NHCONH—), thiourea bonds (—NHCSNH—), sulfonyl ester bonds (—SO₃—), sulfonamido bonds (—SO₂NH—), ureido bonds (—NHCO₂—), thioureido bonds (—NHCSO—), carbonate bonds (—OCO₂—), ether bonds (—O—), thioether bonds (—S—) and amino bonds (—NH—). The size of $L^1$, $L^2$ and $L^3$ in passing from S to D in terms of the number of atoms included is, in the case of $L^1$, 2 to 20, preferably 2 to 10, and in the case of general formula (II), $L^2$ and $L^3$ added together are 4 to 30, preferably 6 to 20. The integers l, m, n, o and p are 1 to 5, 1 to 5, 1 to 15, 3 to 200 and 3 to 500, or preferably 1 to 3, 1 to 2, 1 to 8, 5 to 50 and 10 to 200, respectively.

The novel aromatic diazonium salt used in the present invention can be synthesized, for example, according to the method below.

(i) A method by which an aromatic nitro compound portion and a light-absorbing portion are bonded together; and the resulting compound is reduced to an amine which is then converted into a diazonium compound:

$$(S)_1-(L^1)_m-(D')_n \rightarrow (S)_1-(L^1)_m-(D'')_n \rightarrow \quad (I)$$

$$-(L^2(S))_o-(L^3(D'))_p \longrightarrow -(L^2(S))_o-(L^3(D''))_p \rightarrow \quad (II)$$

D': aromatic nitro compound residue.
D": aromatic amino compound residue.

Reduction and amination can be carried out according to the usual, well-known methods. For example, the method disclosed in the specification of West German Patent No. 1,114,704 (1961) can be used.

(ii) A method by which an amino aromatic diazonium salt be connected to a light-absorbing portion:

In this case, it is necessary for the light absorbing portion to have a functional group to react with the amino group of the aromatic diazonium salt. The functional groups include acidic halide, sulfonyl chloride, isocyanate, thioisocyanate and cyanuric chloride.

The reaction between an amino aromatic diazonium salt and cyanuric chloride is described in the specification of British Patent No. 948,637 (Laid-open 1964).

The anion of the aromatic diazonium salt used according to the present invention is an anion which forms a stable salt with the above diazo compound and which makes the above compound soluble in an organic solvent. These anions include, but are not limited to organic carboxylic acids such as decanoic acid and benzoic acid, and organic phosphoric acids such as phenyl phosphoric acid and sulfonic acids. Typical examples include, but are not limited to aliphatic along with aromatic sulfonic acids such as methanesulfonic acid, chloroethane sulfonic acid, dodecane sulfonic acid, benzenesulfonic acid, toluenesulfonic acid, mesitylene sulfonic acid, anthraquinone sulfonic acid, 2-hydroxy-4-methoxybenzophenone-5-sulfonic acid, hydroquinone sulfonic acid, 4-acetylbenzene sulfonic acid, dimethyl-5-sulfoisophthalate, hydroxy group-containing aromatic compounds such as 2,2',4,4'-tetrahydroxy benzophenone, 1,2,3-trihydroxy benzophenonoe, 2,2',4-trihydroxy benzophenone; halogenated Lewis acids such as hexafluorophosphorix acid and tetrafluoro boric acid; perhalogenated acids such as $ClO_4^-$ and $IO_4^-$; and halogen acids such as $Cl^-$ and $Br^-$.

Some examples of the novel aromatic diazonium compound of the present invention are indicated below. Of course, the present invention is not limited to the below compounds.

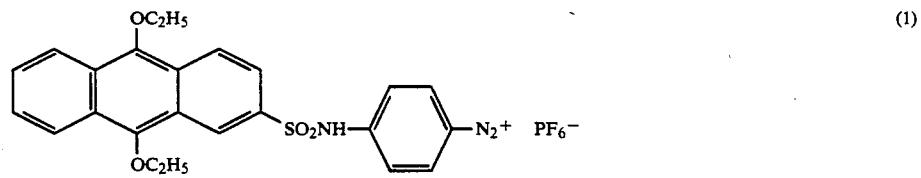

(1)

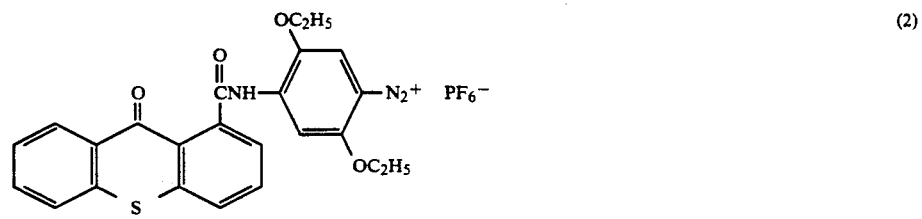

(2)

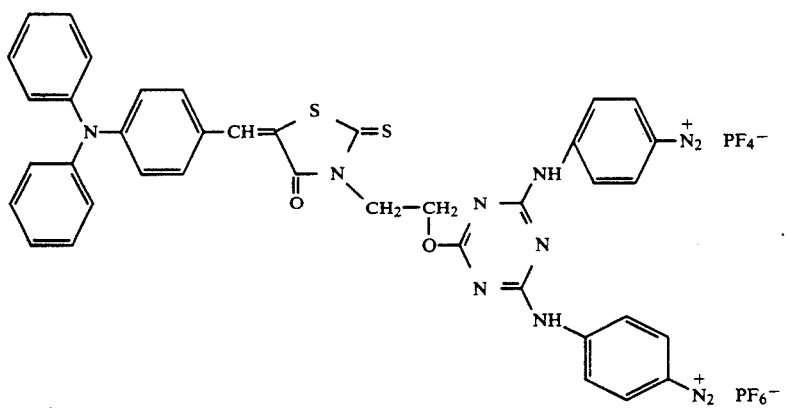
(3)
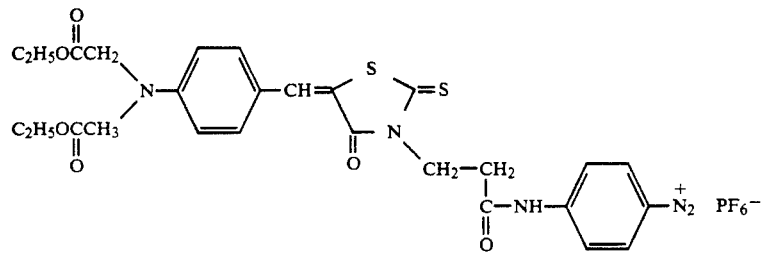
(4)
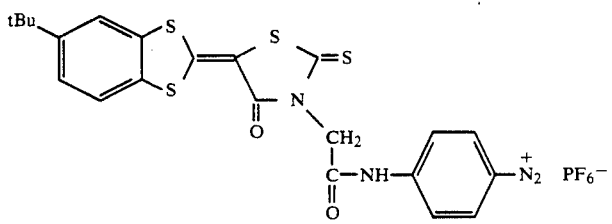
(5)
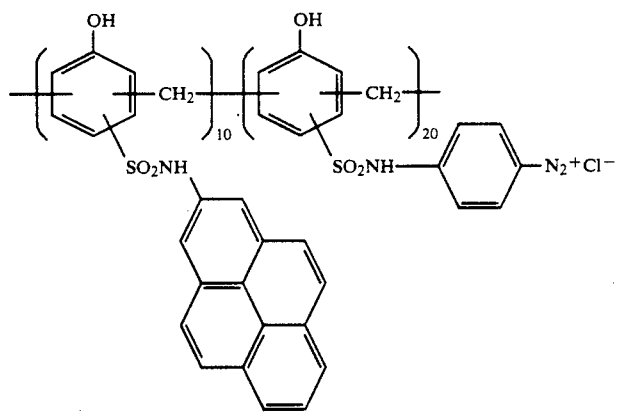
(6)
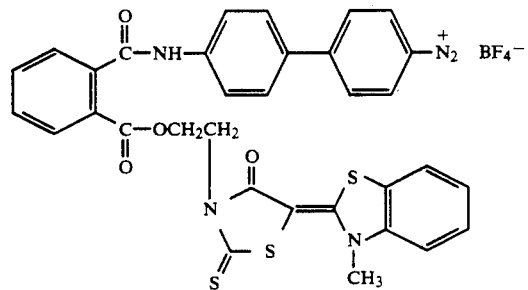
(7)

-continued

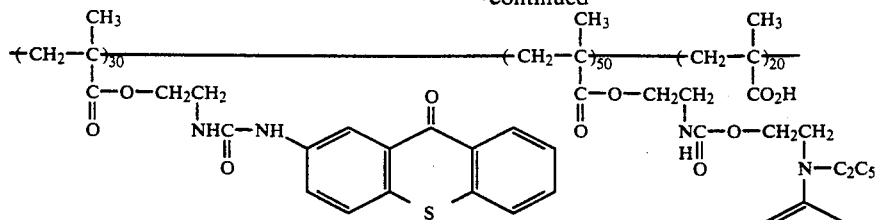
(8)

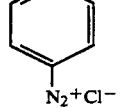

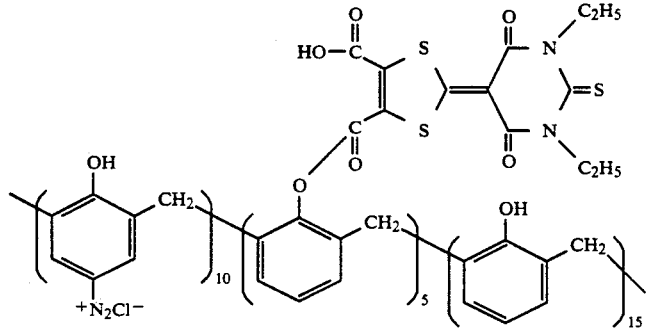
(9)

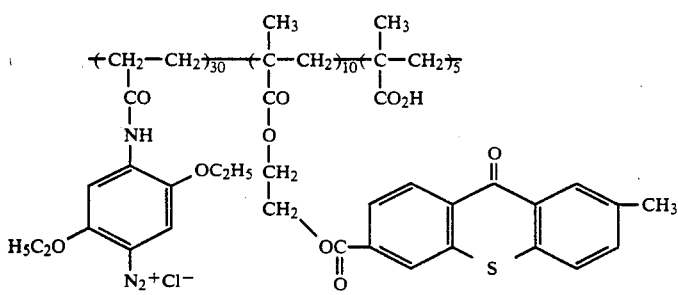
(10)

The light sensitive composition containing the novel diazonium compounds given in general formulas (I) and (II) are used in combination with alkali soluble resins in the light-sensitive layers of light-sensitive printing plates, and in photoresists and the like. When mixed with alkali-soluble resins, the weight of the novel diazonium compounds given in general formulas (I) and (II) is, based on the total weight of the light-sensitive composition, appropriately 5 to 80% by weight, preferably 10 to 40% by weight.

With respect to resins which are soluble in alkali, resins which have this property are novolac resins, for example, phenol/formaldehyde resins; cresol/formaldehyde resins such as m-cresol/formaldehyde resin, p-cresol/formaldehyde resin, p- and m- mixture cresol/-formaldehyde resin, phenol/cresol (p-, m or mixtures of p- and m-)/formaldehyde resins; phenol modified xylene resins; polyhydroxy styrene; polyhalogenated hydroxy styrene; phenolic hydroxy group-containing resins like those described in J.P.KOKAI No. Sho 51-34711; the sulfonamido group-containing acrylic resins described in J.P.KOKAI No. Hei 2-866; urethane resins; and various other high molecular alkali-soluble compounds.

Other acrylic resins may be addition polymers having carboxylic acid groups on the side chains, such as, for example methacrylic acid copolymers, acrylic acid copolymers, itaconic acid copolymers, crotonic acid copolymers, maleic acid, and partially esterified maleic acid copolymers, etc., as disclosed in J.P.KOKAI Nos. Sho 59-44615, Sho 54-92723, Sho 59-53836 and Sho 59-71048 and J.P.KOKOKU (examined publication) Nos. Sho 54-32327, Sho 58-12577 and Sho 54-25957. Also used are acidic cellulose derivatives having carboxylic acid groups on the side chains. In addition, suitably used are addition polymers to which acidic anhydrides have been added. Particularly preferred are copolymers of benzyl (meth)acrylate, (meth)acrylic acid, and optional addition polymerizable vinyl monomers; or copolymers of allyl (meth)acrylate, (meth)acrylic acid, and optional addition polymerizable vinyl monomers.

These alkali-soluble high molecular compounds preferably have an average molecular weight of 500 to 200,000.

Such alkali-soluble high molecular compounds are used in an amount of 80% by weight or less of the total weight of the composition.

The novel diazonium compounds of the present invention can also be used, in combination with unsaturated compounds capable of radical polymerization, as photopolymerizable light-sensitive compositions.

Preferred unsaturated compounds capable of radical polymerization which can be used in the formation of photopolymerizable light-sensitive compositions are, for example, unsaturated esters of polyols, particularly esters of methacrylic or acrylic acid. Specific examples are ethylene glycol diacrylate, glycerin triacrylate, polyester polyacrylate, ethylene glycol dimethacrylate, 1,3-propanediol dimethacrylate, polyethylene glycol dimethacrylate, 1,2,4-butanetriol trimethacrylate, trimethylol ethane triacrylate, pentaerythritol dimethacrylate, pentaerythritol trimethacrylate, pentraerythritol tetramethacrylate, pentaerythritol diacrylate, pentaerythritol triacrylate, pentaerythritol tetraacrylate, dipentaerythritol polyacrylate, 1,3-propane diol diacrylate, 1,5-pentane diol dimethacrylate, polyethylene glycol bis acrylates and bis methacrylates having molecular weight of 200 to 400 and similar compounds.

As unsaturated compounds, one can use unsaturated amides, examples of which are the unsaturated amides of α, ω-diamine and acrylic acid or methacrylic acid, and ethylene bis methacrylamide. However, the photopolymerizable monomers are not limited to the above.

The photopolymerizable monomers are added in an amount of less than 90% by weight of the entire composition.

In order to keep the affect of oxygen low in the light-sensitive compositions of the present invention, it is advantageous to add wax materials such as behenic acid and behenic acid amide.

In the light sensitive composition of the present invention, one can add print-out materials for allowing a visible image to be obtained immediately after exposure, dyes for use as image colorants, and, in addition to the above, fillers. As an examples of visible-image-forming materials which allow a visible image to be obtained immediately after exposure are mixtures of salt forming organic dyes and acid generating compounds which release acid upon exposure to light. Concrete examples are the mixtures of o-naphthoquinonediazide-4-sulfonic acid halides and salt forming organic dyes described in J.P.KOKAI Nos. Sho 50-36209 and Sho 53-8128; or the mixtures of trihalomethyl compounds and salt-forming dyes described in J.P.KOKAI Nos. Sho 53-36223, Sho 54-74728, Sho 60-3626, Sho 61-143748, Sho 61-151644 and Sho 63-58440. Other dyes than the above salt forming organic dyes can be used as image colorlants. Preferable dyes including the salt forming organic dyes include oil soluble dyes and basic dyes. Concrete examples are Oil Yellow-#101, Oil Yellow-#130, Oil Pink-#312, Oil Green BG, Oil Blue-BOS, Oil Blue #603, Oil Black BY, Oil Black BS, Oil Black T-505 (the above all being products of Orient Chemical Inc.), Victoria Pure Blue, Crystal Violet (CI 42555), Methyl Violet (CI 42535), Rhodamine B (CI 45170B), Malachite Green (CI 42000) and Methylene Blue (CI 52015). The dyes described in J.P.KOKAI No. Sho 62-293247 are particularly preferred. The amount of the photoacid generating agent and the dye added to the composition ranges from about 0.3% by weight to about 5% by weight based on the total weight of the composition.

The light-sensitive composition of the present invention is made into a light sensitive lithographic plate by dissolving each of the above components in a solvent in which they dissolve and coating the solution onto a support. The solvents used here may be, used alone or in mixtures, ethylene dichloride, cyclohexanone, methyl ethyl ketone, ethylene glycol monomethyl ether, ethylen glycol monoethyl ether, 2-methoxy ethyl acetate, 1-methoxy-2-propanol, toluene, ethyl acetate, methyl lactate, ethyl lactate, dimethyl sulfoxide, dimethyl acetamide, dimethyl formamide, water, N-methyl pyrrolidone, tetrahydrofurfuryl alcohol, acetone, diacetone alcohol, methanol, ethanol, isopropanol, diethylene glycol dimethyl ether. The concentration of the above components (solid content) is 2 to 50% by weight. Although the weight of the coating differs depending on the particular use, in the case of light-sensitive lithographic printing plates, the amount of the composition coated on the support is generally speaking preferably 0.5 to 3.0 g/m$^2$ after drying. If the weight of the coating is less, the light-sensitivity increases, but the physical properties of the film decrease.

One can add surfactants to the light-sensitive composition of the present invention in order to improve the coating properties, for example, the fluorine atom-containing surfactants described in J.P KOKAI No. Sho 62-170950. Preferred amounts added are 0.01 to 1% by weight of the entire light-sensitive composition, more preferably, 0.05 to 0.5% by weight.

When the above light-sensitive composition is used as a coating, a plate having dimensional stability is used as a support. One can name as the dimensionally stable plates, paper, paper laminated by plastic (for example polyethylene, polypropylene, polystyrene, etc.); metal plates such as aluminum (including aluminum alloys), zinc and copper; and plastic films such as cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate and polyvinyl acetal; and paper and plastic films on which the above metals have been laminated or deposited.

When making up light-sensitive lithographic printing plates, aluminum is particularly preferred because it has remarkable dimensional stability and it is inexpensive. Furthermore, also preferred is a composite sheet such as the aluminum sheet bonded onto a polyethylene terephthalate film as described in J.P.KOKOKU No. Sho 48-18327.

It is preferred to carry out surface treatments on supports having metal or particularly aluminum surfaces. Such treatments include graining treatments, immersion treatments in aqueous solutions such as sodium silicate, potassium fluorozirconate and phosphate, and anodization treatments.

Appropriate developing solutions for the light-sensitive compositions of the present invention are aqueous alkali solutions such as sodium silicate, potassium silicate, sodium hydroxide, potassium hydroxide, lithium hydroxide, trisodium phosphate, disodium hydrogenphosphate, triammonium phosphate, diammonium hydrogen phosphate, sodium metasilicate, sodium bicarbonate, aqueous ammonia and tetramethyl ammonium hydroxide. The above can be added to make concentrations of 0.1 to 10% by weight, preferably 0.5 to 5% by weight.

The light source used for exposure can be mercury vapor lamps of various types such as ultra hi9h pressure, intermediate pressure and low pressure; carbon arc lamps; chemical lamps; xenon lamps; tungsten lamps; metal halide lamps; various types of lasers such as visible or near infra red; fluorescent lamps; and sunlight.

The light-sensitive composition of the present invention has high sensitivity to light in a broad wavelength region from the ultraviolet region to the visible region.

The following working examples further explain the present invention, but do no limit the invention.

SYNTHETIC EXAMPLE 1

The synthesis of diazonium compound (4) is conducted according to the following route.

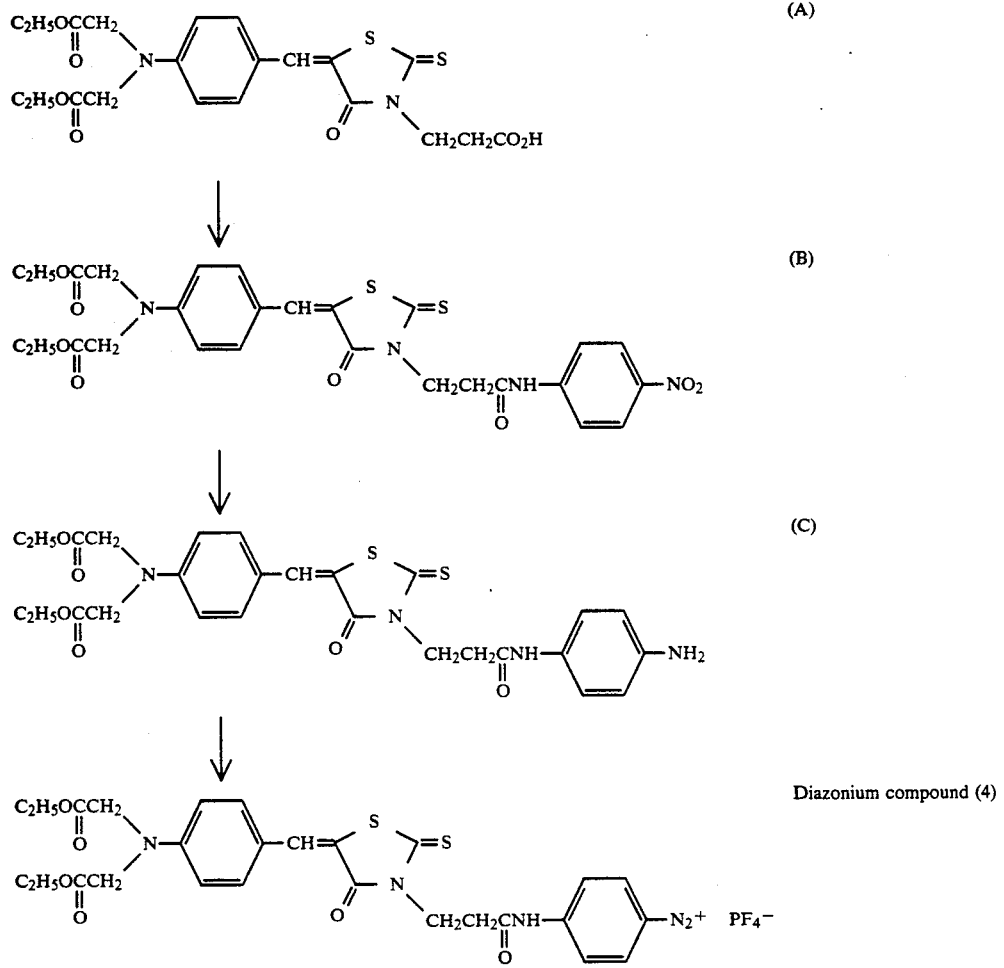

(A)

(B)

(C)

Diazonium compound (4)

Synthesis of Compound (B)

Cyclohexyl carbodiimide (5.4 g) was dissolved in 200 ml of methylene chloride and cooled to a temperature of 0° C. Compound (A) (10 g) was added, and after 3 min. stirring, the solution temperature was allowed to rise to room temperature and the solution was further stirred for 15 min. p-Nitro aniline (3.1 g) was added and stirring was continued overnight. The reaction mixture was poured into water and the mixture was extracted with 500 ml of ethyl acetate. The extract was concentrated to 200 ml and the resulting crystals were obtained by filtration.

| Yield: | 4.1 g |
|---|---|
| Melting Point: | 188° C. |
| Infrared absorption spectra: | 1630 cm$^{-1}$ (—CONH—) |
| | 1740 cm$^{-1}$ (—COOC$_2$H$_5$) |

Synthesis of Compound (C)

Compound (B) (6 g), ammonium chloride (0.5 g), isopropanol (300 ml), and water (30 ml) were added together, and refluxed with the addition of heat for 30 min. under a stream of nitrogen gas. Thereafter, 0.6 g of iron powder was slowly added and refluxed with the addition of heat for 2 hours. After the reaction was completed, the iron powder was filtered and, when the filtrate was cooled, crystals precipitated.

Yield: 3.2 g
Melting Point: 180° C.
Infrared absorption spectra: 3500 and 3400 cm$^{-1}$ (—NH$_2$).

Synthesis of Diazonium Compound (4)

After compound (C) (5.4 g) was dissolved in 100 ml of a 5% hydrochloric acid solution, it was cooled to 0° C. While this aqueous solution was stirred, a solution of 0.69 g sodium nitrite in 5 ml of water was added a little bit at a time. After continuing stirring for 30 min., a solution of 2.0 g potassium hexafluoro phosphate in 50 ml water was added while stirring. The resulting yellow precipitate was filtered and dried.

Yield 4.0 g
Infrared spectra: 2260 cm$^{-1}$ (—N$_2^+$),

WORKING EXAMPLE 1

A light-sensitive lithographic plate was made by forming a light-sensitive layer by coating the following light-sensitive solution onto a grained and anodized aluminum plate so that the coating weight after drying was 1.5 g/m$^2$.

| | |
|---|---|
| Phenol resin (a polycondensate of phenol and formaldehyde) (available from Sumitomo Durez Inc.) | 0.60 g |
| Diazonium Compound (4) | 0.20 g |
| N-methyl pyrrolidone | 6 g |
| Ethyl cellosolve acetate | 4 g |

A light sensitive lithographic printing plate made in this manner was exposed to light of Jetlight 2000 (available from Oak Co.) through an SC-46 filter which cut light under 460 nm.

Sensitivity measurements were made using a Fuji PS Step guide (Fuji Phot Film Co., Ltd., a step tablet wherein the initial step light transmission density of 0.05 progressively increases by 0.15 to a step 15). When the plate was developed in a 5.26% aqueous solution (pH=12.7) of sodium silicate with a molar ratio of SiO$_2$/Na$_2$O of 1.74, the light-sensitive layer remained until step 9, and, from step 10, the light-sensitive layer was completely removed and a negative image was obtained.

After the plate was developed in this manner, and after the steps of sufficiently washing with water and gumming-up, printing was carried out in the usual manner, and 10,000 printed sheets could be obtained.

COMPARATIVE EXAMPLE 1

Diazonium Compound (4) was replaced with the following light-sensitive substance, and, otherwise, a light-sensitive lithographic printing plate was made by completely the same method as Working Example 1.
Light-sensitive substance (A) 0.15 g
(B) 0.065 g

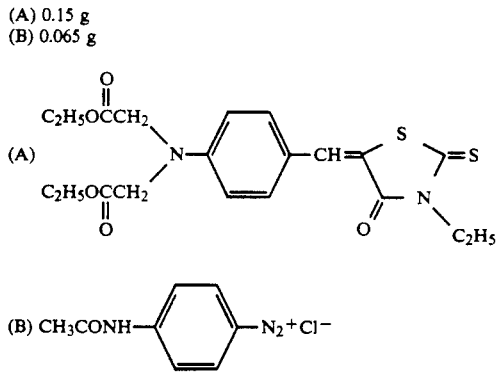

Development was carried out by the same method of Working Example 1, but the entire surface of the light-sensitive layer was removed and a negative image could not be obtained.

What is claimed is:

1. A light-sensitive composition, said composition comprising a sensitizing amount of a compound or polymer, wherein said compound is being represented by the following general formula (I):

$$(S)_l-(L^1)_m-(D)_n \quad (I);$$

and said polymer comprises a moiety represented by the following general formula (II):

$$-(L^2(S))_o-(L^3(D))_p- \quad (II);$$

wherein D is an aromatic diazonium salt group, S is a light absorbing group which is a residue of a sensitizing dye for trichloromethyl-s-triazine photopolymerization initiators or azinium salt photopolymerization initiators, and which has an absorption coefficient or more than 1000 at wavelengths longer than 300 nm, $L^1$, $L^2$ and $L^3$ are connecting groups connecting S and D, provided that S and D are not conjugated by $L^1$, $L^2$ and $L^3$, l is an integer of 1 to 5, m is an integer of 1 to 5, n is an integer of 1 to 15, o is an integer of 3 to 200, and p is an integer of 3 to 500.

2. The light-sensitive composition according to claim 1, wherein the light absorbing group is a light-absorbing residue of a dye selected from merocyanine dyes, cyanine dyes, acridine dyes, thiapyrylium dyes, arylidene dyes, multi nucleus aromatic compounds, xanthene dyes, coumarin compounds, hetero aromatic compounds, amino aromatic compounds, porphyrin dyes and phthalocyanine dyes.

3. The light-sensitive composition according to claim 2, wherein the light absorbing group is a light-absorbing residue of a dye selected from merocyanine dyes, cyanine dyes, acridine dyes, multi nucleus aromatic compounds, xanthene dyes, coumarin compounds, hetero aromatic compounds and arylidene dyes of formula (III):

$$R-(CH=CH)_n-CH=C(G^1)(G^2) \quad (III)$$

wherein
R represents a substituted or unsubstituted aromatic ring, or a heteroaromatic ring having 6 to 20 carbon atoms;
$G^1$ and $G^2$ may be the same or different and each may represent a hydrogen atom, a cyano group, an alkoxy carbonyl group, a substituted alkoxy carbonyl group, an aryloxy carbonyl group, a substituted aryloxy carbonyl group, an acyl group, a substituted acyl group, an aryl carbonyl group, a substituted aryl carbonyl group, an alkylthio group, an arylthio group, an alkyl sulfonyl group, an aryl sulfonyl group or a fluoroalkyl sulfonyl group, provided that $G^1$ and $G^2$ are not hydrogen atoms at the same time, and $G^1$ and $G^2$ may also be in the form of a ring of carbon atoms bound together with non-metallic elements; and
n is 0 or 1.

4. The light-sensitive composition according to claim 3, wherein the light absorbing group is an arylidene residue according to general formula (III), wherein $G^1$ and $G^2$ together form a barbituric acid group or a rhodanine group.

5. The light-sensitive composition according to claim 4, wherein $G^1$ and $G^2$ together form 1,3-diethyl-2-thiobarbituric acid group or 3-ethyl rhodanine group.

6. The light-sensitive composition according to claim 1, wherein the aromatic diazonium salt portion is selected from the group consisting of benzenediazonium salt, naphthalene diazonium salt, biphenyldiazonium salt and anthraquinone diazonium salt.

7. The light-sensitive composition according to claim 6, wherein the aromatic diazonium salt portion has a substituent selected from the group consisting of alkoxy groups, substituted thiol groups, amino groups, carboalkoxy groups and halogen atoms.

8. The light-sensitive composition according to claim 7, wherein the aromatic diazonium salt portion has a substituent selected from the group consisting of methoxy, ethoxy, butoxy, methyl thio, phenyl thio, dimethyl amino, diethyl amino, phenyl amino, carbomethoxy groups and halogen atoms.

9. The light-sensitive composition according to claim 1, wherein $L^1$, $L^2$ and $L^3$ are selected from the group consisting of ester bonds (—$CO_2$—), amido bonds (—CONH—), urea bonds (—NHCONH—), thiourea bonds (—NHCSNH—), sulfonyl ester bonds (—$SO_3$—), sulfonamido bonds (—$SO_2$NH—), ureido bonds (—$NHCO_2$—), thioureido bonds (—NHCSO—), carbonate bonds (—$OCO_2$—), ether bonds (—O—), thioether bonds (—S—) and amino bonds (—NH—).

10. The light-sensitive composition according to claim 9, wherein $L^1$ contains from 2 to 20 atoms, and $L^2$ and $L^3$ together contain from 4 to 30 atoms.

11. The light-sensitive composition according to claim 10, wherein $L^1$ contains from 2 to 10 atoms, and $L^2$ and $L^3$ together contain from 6 to 20 atoms.

12. The light-sensitive composition according to claim 1, wherein l is 1 to 3, m is 1 to 2, n is 1 to 8, o is 5 to 50 and p is 10 to 200.

13. The light-sensitive composition according to claim 1, wherein an anion of the diazonium salt is selected from the group consisting of organic carboxylic acids, organic phosphoric acids and sulfonic acids.

14. The light-sensitive composition according to claim 1, wherein an anion of the diazonium salt is selected from the group consisting of methanesulfonic acid, chloroethane sulfonic acid, dodecane sulfonic acid, benzenesulfonic acid, toluenesulfonic acid, mesitylene sulfonic acid, anthraquinone sulfonic acid, 2-hydroxy-4-methoxybenzophenone-5-sulfonic acid, hydroquinone sulfonic acid, 4-acetylbenzene sulfonic acid, dimethyl-5-sulfoisophthalate, 2,2',4,4'-tetrahydroxy benzophenone, 1,2,3-trihydroxy benzophenone, 2,2',4-trihydroxy benzophenone, hexafluorophosphoric acid, tetrafluoro boric acid, $ClO_4^-$, $IO_4^-$, $Cl^-$ and $Br^-$.

15. The light-sensitive composition according to claim 1, wherein the diazonium compound is contained in an amount of 5 to 80% by weight based on the total weight of the composition.

16. The light-sensitive composition according to claim 15, wherein the diazonium compound is contained in an amount of 10 to 40% by weight based on the total weight of the composition.

17. A light-sensitive composition comprising, in admixture, an alkali soluble resin and a sensitizing amount of a compound or polymer, wherein said compound is represented by the following general formula (I):

$$(S)_l-(L^1)_m-(D)_n \qquad (I);$$

and said polymer comprises a moiety represented by the following general formula (II):

$$-(L^2(S))_o-(L^3(D))_p- \qquad (II);$$

wherein D is an aromatic diazonium salt group, S is a light absorbing group which is a residue of a sensitizing dye for trichloromethyl-s-triazine photopolymerization initiators or azinium salt photopolymerization initiators, and which has an absorption coefficient of more than 1000 at wavelengths longer than 300 nm, $L^1$, $L^2$ and $L^3$ are connecting groups connecting S and D, provided that S and D are not conjugated by $L^1$, $L^2$ and $L^3$, l is an integer of 1 to 5, m is an integer of 1 to 5, n is an integer of 1 to 15, o is an integer of 3 to 200, and p is an integer of 3 to 500.

18. The light-sensitive composition according to claim 17, wherein said alkali soluble resin is contained in an amount of less than 80% by weight based on the total weight of the composition and the diazonium compound is contained in an amount of 5 to 80% by weight based on the total weight of the composition.

19. The light-sensitive composition according to claim 17, wherein the alkali soluble resin is selected from the group consisting of phenol/formaldehyde resins; cresol/formaldehyde resins selected from m-cresol/formaldehyde resin, p-cresol/formaldehyde resin, p- and m- mixture cresol/formaldehyde resin, phenol/cresol (p-, m- or mixtures of p- and m-)/formaldehyde resins; phenol modified xylene resins; polyhydroxy styrene; polyhalogenated hydroxy styrene; phenolic hydroxy group-containing resins; sulfonamido group containing acrylic resins; urethane resins; addition polymers having carboxylic acid groups on the side chains; and acidic cellulose derivatives having carboxylic acid groups on the side chains.

20. The light-sensitive composition according to claim 19, wherein the alkali soluble resin is selected from the group consisting of copolymers of benzyl (meth)acrylate, (meth)acrylic acid, and optional addition polymerizable vinyl monomers; and copolymers of allyl (meth)acrylate, (meth)acrylic acid, and optional addition polymerizable vinyl monomers.

21. A photopolymerizable light-sensitive composition comprising, together in admixture, a radical polymerizable unsaturated compound and a sensitizing amount of a compound or polymer, wherein said compound is represented by the following general formula (I):

$$(S)_l-(L^1)_m-(D)_n \qquad (I);$$

and said polymer comprises a moiety represented by the following general formula (II):

$$-(L^2(S))_o-(L^3(D))_p- \qquad (II);$$

wherein D is an aromatic diazonium salt group, S is a light absorbing group which is a residue of a sensitizing dye for trichloromethyl-s-triazine photopolymerization initiators or azinium salt photopolymerization initiators, and which has an absorption coefficient of more than 1000 at wavelengths longer than 300 nm, $L^1$, $L^2$ and $L^3$ are connecting groups connecting S and D, provided that S and D are not conjugated by $L^1$, $L^2$ and $L^3$, l is an integer of 1 to 5, m is an integer of 1 to 5, n is an integer of 1 to 15, o is an integer of 3 to 200, and p is an integer of 3 to 500.

22. The photopolymerizable light-sensitive composition according to claim 21, wherein the unsaturated compound is an unsaturated ester of a polyol and acrylic acid or methacrylic acid.

23. The photopolymerizable light-sensitive composition according to claim 21, wherein the unsaturated compound is contained in an amount of less than 90% by weight based on the total weight of the composition and the compound of formula (I) or polymer of formula (II) is contained in an amount of 5 to 80% by weight based on the total weight of the composition.

24. A light-sensitive lithographic printing plate comprising a support having provided thereon a light-sensitive layer comprising together, in admixture, a sensitizing amount of a compound or polymer, wherein said compound is represented by the following general formula (I):

$$(S)_l-(L^1)_m-(D)_n \qquad (I);$$

and said polymer comprises a moiety represented by the following general formula (II):

$$-(L^2(S))_o-(L^3(D))_p-  \quad (II);$$

wherein D is an aromatic diazonium salt group, S is a light absorbing group which is a residue of a sensitizing dye for trichloromethyl-s-triazine photopolymerization initiators or azinium salt photopolymerization initiators, and which has an absorption coefficient of more than 1000 at wavelengths longer than 300 nm, $L^1$, $L^2$ and $L^3$ are connecting groups connecting S and D, provided that S and D are not conjugated by $L^1$, $L^2$ and $L^3$, l is an integer of 1 to 5, m is an integer of 1 to 5, n is an integer of 1 to 15, o is an integer of 3 to 200, and p is an integer of 3 to 500; and an alkali soluble resin.

25. A light-sensitive lithographic printing plate comprising a support having provided thereon a light-sensitive layer comprising together, in admixture, a sensitizing amount of a compound or polymer, wherein said compound is represented by the following general formula (I):

$$(S)_l-(L^1)_m-(D)_n \quad (I);$$

and said polymer comprises a moiety represented by the following general formula (II):

$$-(L^2(S))_o-(L^3(D))_p- \quad (II);$$

wherein D is an aromatic diazonium salt group, S is a light absorbing group which is a residue of a sensitizing dye for trichloromethyl-s-triazine photopolymerization initiators or azinium salt photopolymerization initiators, and which has an absorption coefficient of more than 1000 at wavelengths longer than 300 nm, $L^1$, $L^2$ and $L^3$ are connecting groups connecting S and D, provided that S and D are not conjugated by $L^1$, $L^2$ and $L^3$, l is an integer of 1 to 5, m is an integer of 1 to 5, n is an integer of 1 to 15, o is an integer of 3 to 200, and p is an integer of 3 to 500; and alkali soluble resin; and a radical-polymerizable, unsaturated compound.

* * * * *